United States Patent [19]

Plante

[11] 4,423,636

[45] Jan. 3, 1984

[54] ARTICULATED TEST PROBE MECHANISM WITH FLUID BEARING IN TEST ROLL GAP

[75] Inventor: Arcade J. Plante, Center Valley, Pa.

[73] Assignee: Bethlehem Steel Corporation, Bethlehem, Pa.

[21] Appl. No.: 328,772

[22] Filed: Dec. 8, 1981

[51] Int. Cl.³ .............................................. G01N 29/04
[52] U.S. Cl. ...................................... 73/622; 73/640; 324/262
[58] Field of Search ................ 73/618, 622, 633, 634, 73/640; 324/262

[56] References Cited

U.S. PATENT DOCUMENTS

| | | | |
|---|---|---|---|
| 3,586,967 | 6/1971 | Peyrot et al. | 324/40 |
| 3,741,003 | 6/1973 | Gunkel | 73/644 |
| 3,884,076 | 5/1975 | Studer | 73/37.6 |
| 3,952,582 | 4/1976 | Graham et al. | 73/644 |
| 4,213,183 | 7/1980 | Barron et al. | 73/634 X |
| 4,258,319 | 3/1981 | Shimada et al. | 324/262 |

OTHER PUBLICATIONS

P. Keller, "A New Technique For Noncontact Temperature Measurement of Rotating Rolls," *Iron and Steel Engineer*, May, 1980, pp. 42–44.

*Primary Examiner*—James J. Gill
*Attorney, Agent, or Firm*—John I. Iverson; William B. Noll; John J. Selko

[57] ABSTRACT

A nondestructive eddy current or ultrasonic articulated probe mechanism automatically detects rolling mill roll surface defects for use with a defect test system. The articulated probe mechanism is mounted on a traversing roll grinder carriage, is automatically positioned over the test roll, and has a probe head with controlled fluid bearing, air or liquid, to automatically maintain probe head-to-test roll gap. One or multiple eddy current, or ultrasonic, probes in the head generate anomoly test signals which, together with a probe head temperature sensor signal, are suitable for processing in an appropriate test instrument.

3 Claims, 6 Drawing Figures

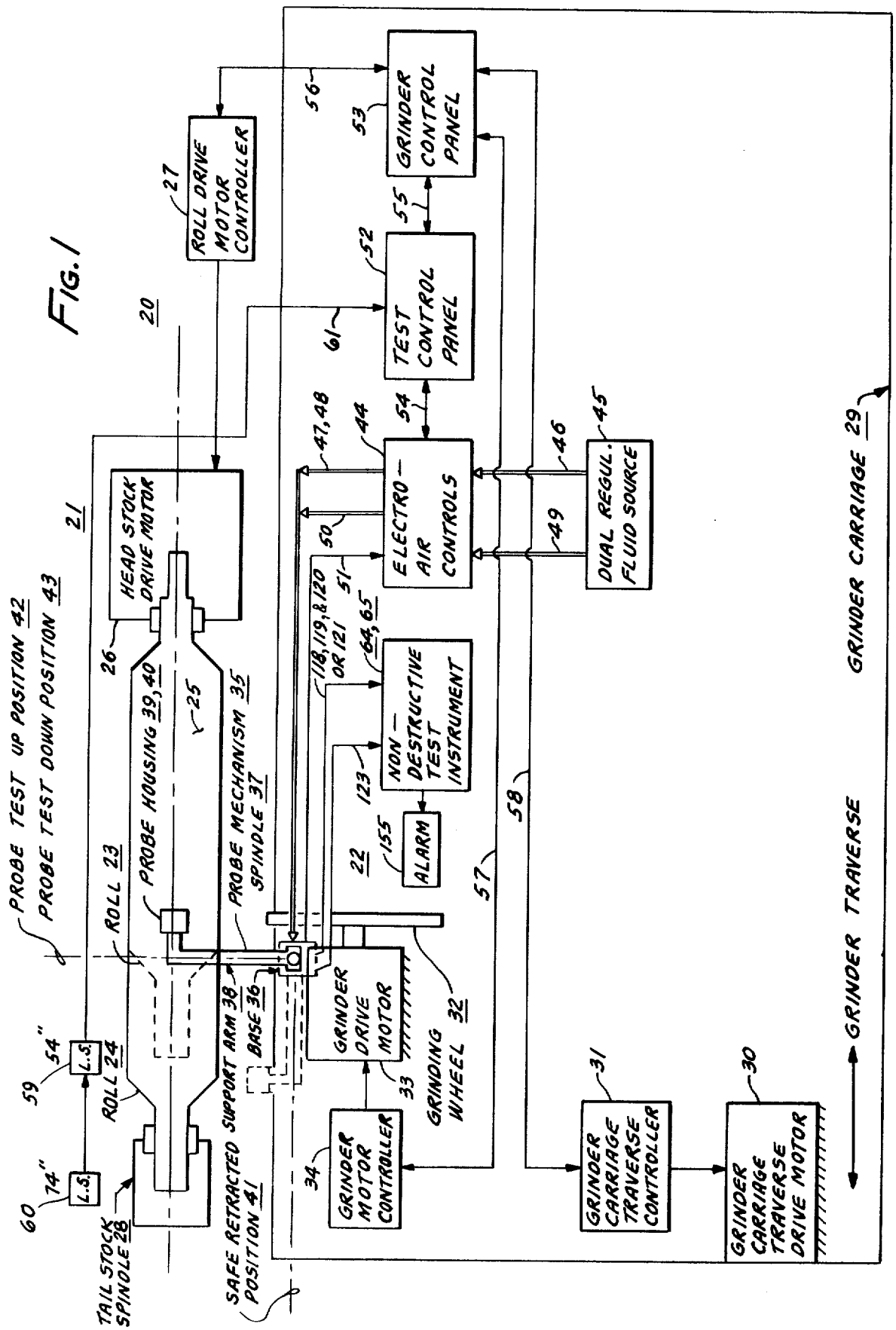

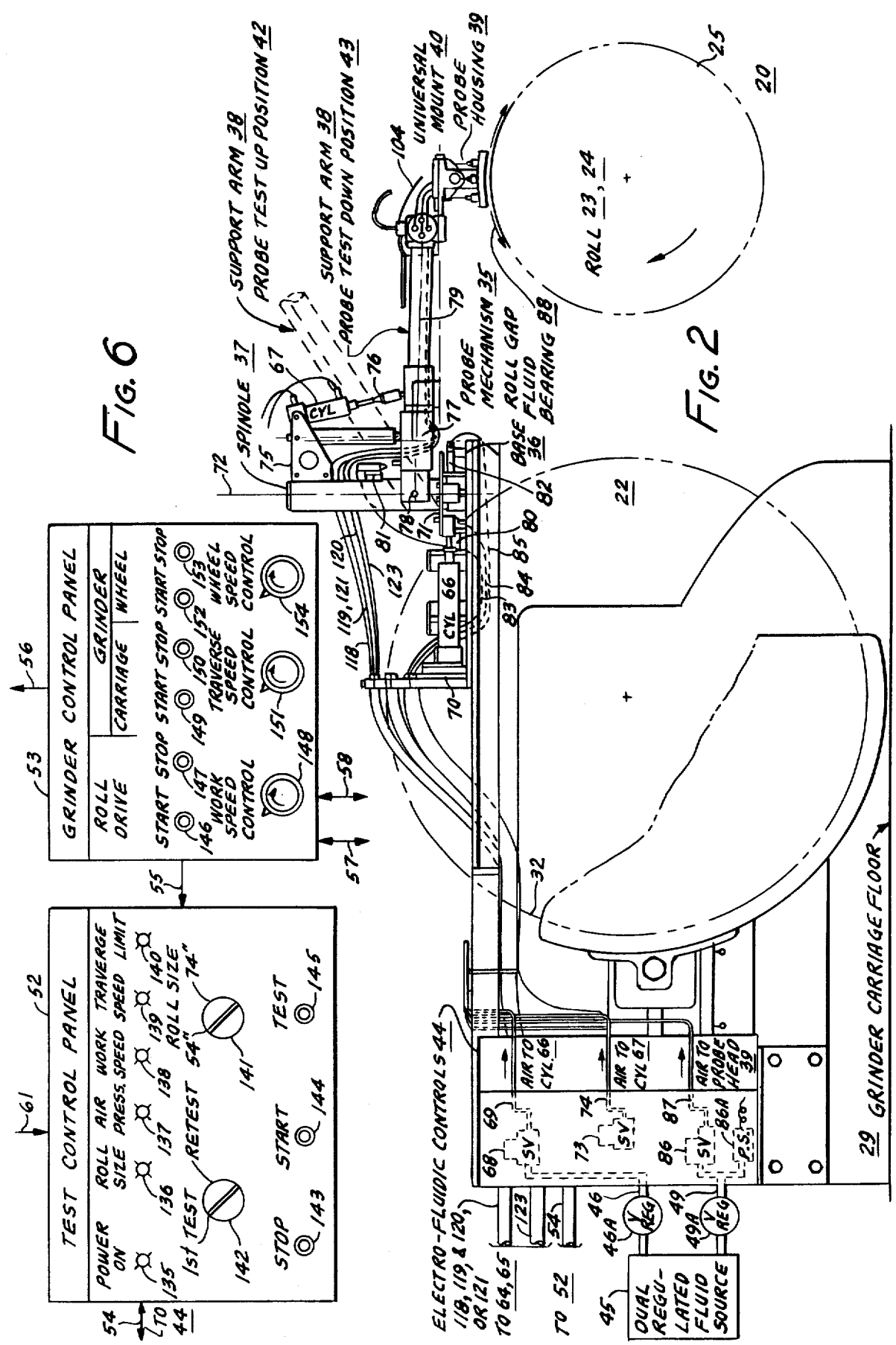

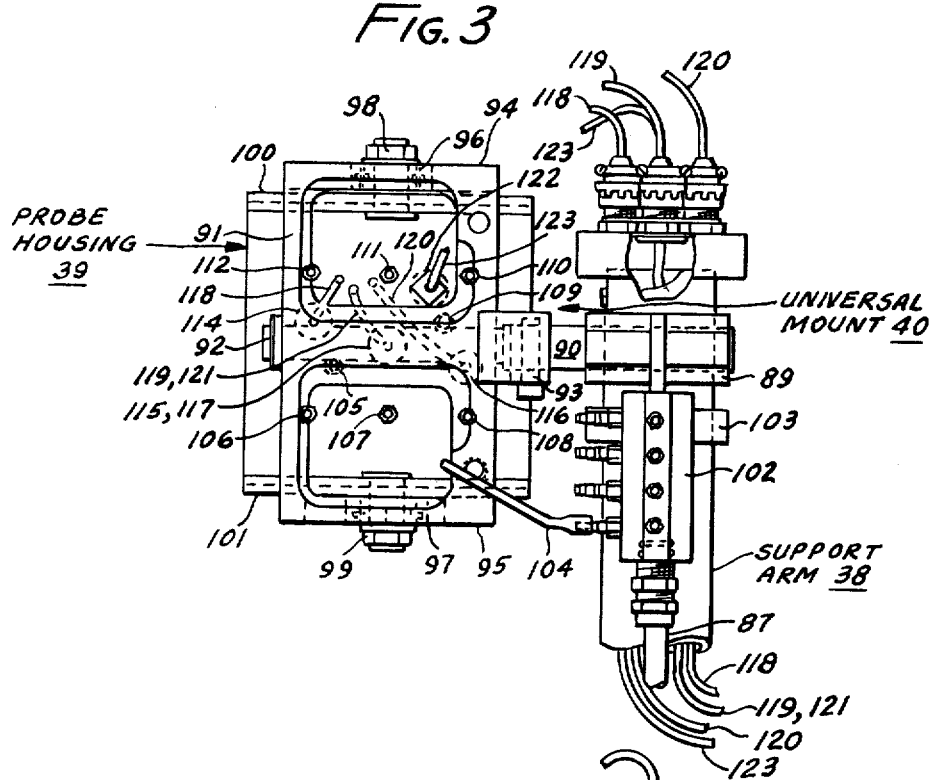
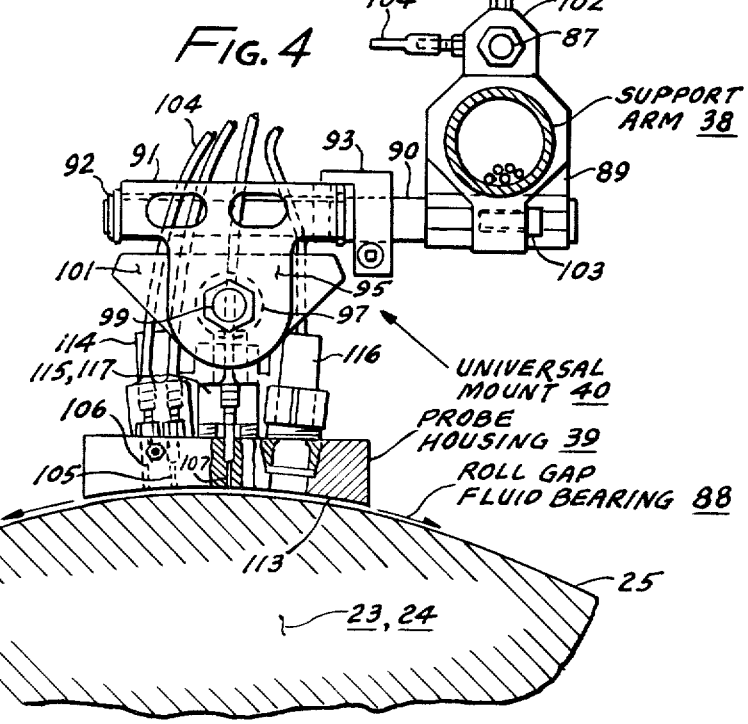

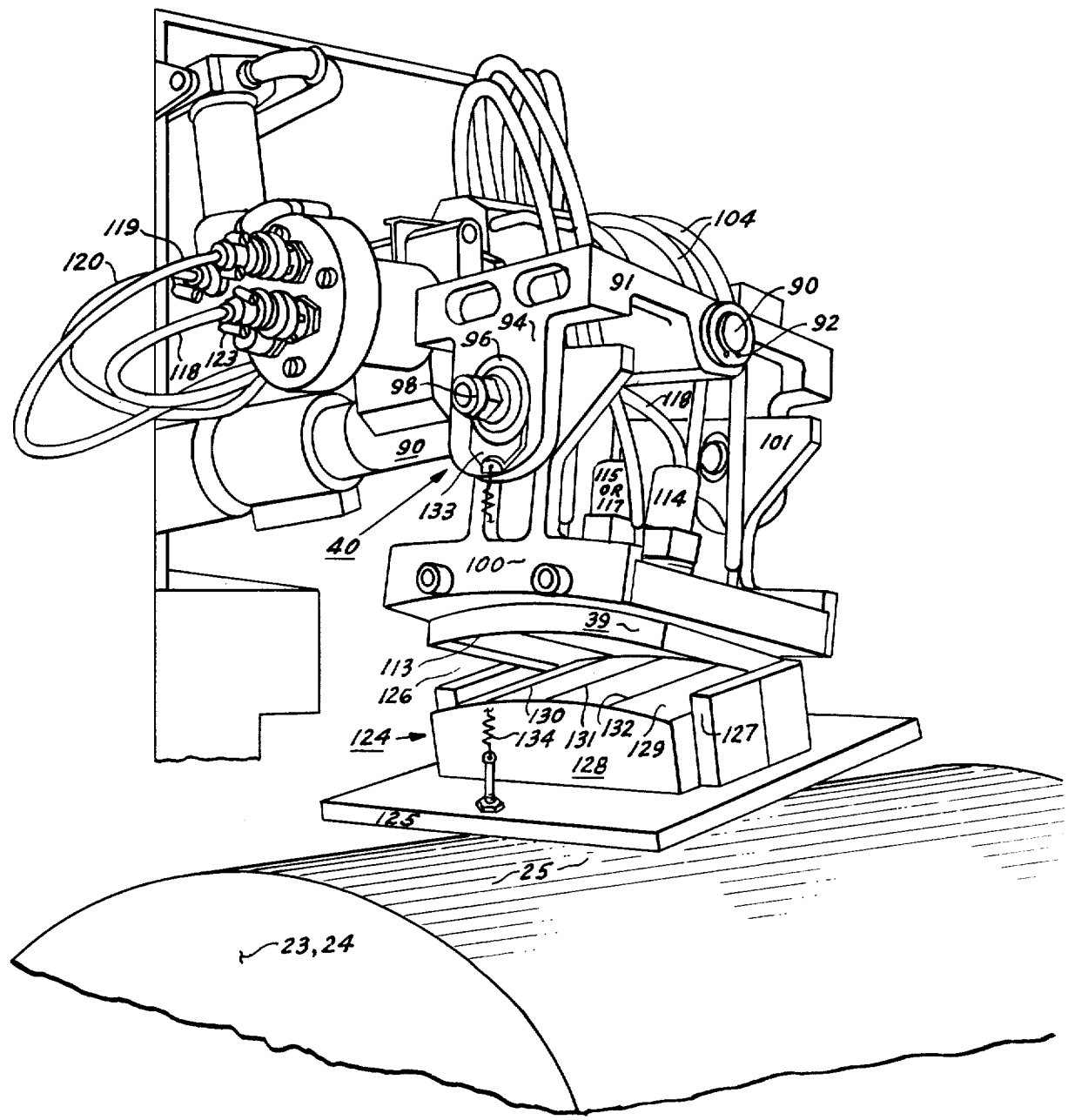

ARTICULATED TEST PROBE MECHANISM WITH FLUID BEARING IN TEST ROLL GAP

BACKGROUND OF THE INVENTION

This invention relates to a nondestructive eddy current or ultrasonic articulate probe mechanism for automatically detecting rolling mill roll surface defects using a fluid bearing, air or liquid, in a probe head-to-test roll gap, or simply the roll gap.

DESCRIPTION OF THE PRIOR ART

Cast and forged steel rolls used in high-speed tandem rolling mills to make flat steel products, for example, represent a significant part of procurement and maintenance costs of these mills. Mill records show that theoretical roll availability is reduced by as much as fifty percent before such rolls fail or have to be scrapped. Observations of failed tandem mill rolls indicate many failures originate at surface damage not visually detected by a grinder operator and removed during normal reconditioning. In a tandem mill environment, roll failure is caused by surface spalling and radial shelf cracking type of defects.

Spalling and shelf cracking defects in rolls are caused by a combination of high end pressures, wear conditions, work hardening and internal hardness variations. Such conditions may arise in production operations from untrimmed butt welds and laminations passing through tandem mills; secondary damage from debris of another roll failure; unusual mill operations that overstress the roll surface; or improper off-line handling. Oftimes, rolls subject to spalling and cracking defects are prematurely scrapped when reground to remove such defects and reused only once or twice in a mill after an accident.

Rolls with surface spall and crack defects make an unwanted impression on the surface of the rolled product. This condition is cause for scrapping of the rolled product, as well as for more frequent roll changes and roll surface grinding. All of these situations cause expensive downtime delays and adversely affect mill output and profitability.

Presently, the most common method of detecting rolling mill roll surface defects, whenever they occur, is visual observation of the roll surface by a grinder operator at an off-line roll grinder station. Normally, a grinder operator may not observe surface crack defects as small as about ⅛ inch long and 0.020 inch deep which should be classified as unacceptable to prevent roll failure. Oversight of unacceptable defects with this visual method is a serious problem and must be overcome if mill output and profits are to be increased.

Some attempt has been made to use laboratory types of nondestructive (NDT) eddy current, or ultrasonic, test instruments in a steel rolling mill environment at an inspection station aside from the roll grinder station with only limited success. Such test apparatus includes a simple uncompensated eddy current test probe, for example, which is manually adjusted so that a wearing block at the probe end will contact the roll surface and attempt to maintain a constant roll gap while the probe traverses the roll surface. Probe output signals are sensitive to roll gap undulations, wearing block noise, probe ambient temperature and roll metallurgy and hardness variations, as well as the roll surface defects to be detected. Thus, the probe outputs a complex analog test signal pattern to a conventional nondestructive eddy current or ultrasonic test instrument, which does not compensate for the variables added to the analog defect signal.

The prior art complex analog test signal from the probe must be processed in a test instrument and evaluated by a separate inspector skilled in NDT test and analysis methods. This must be done while the roll is at the inspection station in order to ascertain the existance of roll surface defect characteristics among the complex test pattern. After an interpretation is made, the test roll must be transferred back and forth between roll inspection and roll grinding stations, then reinspected until the roll surface is acceptably reconditioned or the entire roll is discarded. This arrangement of test, grind and retest is not only an expensive test method, but it consumes a lot of extra production down time as well. Commercial test probe equipment for automatically detecting roll surface defects is unavailable.

SUMMARY OF THE INVENTION

An object of this invention is to provide an improved eddy current, or ultrasonic, probe mechanism for automatically testing rolling mill roll surface defects.

Another object of this invention is to provide an improved nondestructive eddy current or ultrasonic probe mechanism for testing roll surface defects without requiring a roll test operator to manually adjust test probe position to obtain valid test signals and results.

Still another object of this invention is to provide an improved nondestructive eddy current or ultrasonic probe mechanism for testing roll surface defects which permit defect detection and roll grinding operations to be carried out without interchanging a test roll between roll test inspection and roll grinding stations.

The foregoing objects are attained by providing a nondestructive eddy current or ultrasonic articulated probe mechanism for automatically detecting rolling mill roll surface defects for use with a defect test system. The articulated probe mechanism is mounted on a traversing roll grinder carriage in line with the grinding wheel, is automatically positioned over the test roll at the grinding wheel in response to control means initiated by the grinder operator, and has a probe head with a controlled fluid bearing, air or liquid, to automatically maintain probe head-to-test-roll gap, thereby avoiding a roll gap wearing block. One or multiple nondestructive eddy current or ultrasonic probes in the head generate anomoly test signals which, together with a probe temperature sensor are suitably processed in an appropriate test instrument.

BRIEF DESCRIPTION OF THE DRAWINGS

FIG. 1 is a plan view block diagram of the overall invention showing the articulated probe mechanism mounted on a roll grinder carriage, over a test roll, and including controls for automatically positioning the probe mechanism.

FIG. 2 is an elevational view of the articulated probe mechanism of this invention mounted on a grinder carriage and including schematic electro-fluidic connections thereto.

FIG. 3 is an enlarged plan view of the probe head portion of this invention

FIG. 4 is an enlarged lateral cross-sectional view of the probe head at a test roll surface.

FIG. 5 is an isometric view of the probe head, including a mechanical artificial probe calibrator.

FIG. 6 covers pictorial elevation views of test control and grinder operator control panels for automatically controlling the position of the probe mechanism over the test roll.

DESCRIPTION OF THE PREFERRED EMBODIMENTS

Referring to the drawings, particularly FIGS. 1-6, there is shown the automatically controlled articulated probe mechanism of the nondestructive (NDT) eddy current or ultrasonic testing system for automatically inspecting rolling mill roll surface for defects. The term "nondestructive testing (NDT)" used herein applied to both well known eddy current and ultrasonic test and analysis methods. Similarly, the term "fluid bearing" applies herein to both air and liquid roll gap media.

FIG. 1 shows a plan view in block diagram form of a typical rolling mill roll grinder station 20 where roll lath 21 is operatively associated with roll grinder 22 in both testing and grinding of either 137 cm. (54") or 188 cm. (74") long test rolls 23,24, respectively, around the circumference and lengthwise of test roll surface 25. Roll lathe 21 includes a variable-speed head stock with drive motor 26 under control of roll drive motor controller 27, and further includes a tail stock spindle 28 adjustable to hold either test roll.

Roll grinder 22 includes traversing grinder carriage 29 is driven parallel to the longitudinal axis of test rolls 23,24 by grinder carriage traverse drive motor 30 in response to grinder carriage traverse controller 31. A conventional roll grinder 22 is used which includes a grinding wheel 32 powered by variable-speed grinder drive motor 33 and is controlled by grinder motor controller 34. Grinder drive motor 33 is mounted on the floor of traverse carriage 29 in such manner that grinding wheel 32 may be engaged with the test roll surface 25 throughout the length of either test roll 23,24 while the grinder carriage 29 traverses either right-to-left or left-to-right as shown.

Also mounted on the traversing grinder carriage 29 in line with roll grinding wheel 32 is articulated probe mechanism 35 which is automatically positioned with constant constant fluid bearing roll gap over test roll surface 25 as shown more clearly in FIGS. 2-6. Articulated probe mechanism 35 comprises a base 36, an upright spindle 37 affixed rotatably to base 36, an articulated support arm 38 pivotally attached to rotatable spindle 37, and a probe housing 39 attached through universal mount 40 to the end of support arm 38 so as to be in line with grinding wheel 32 during testing and grinding operations.

Articulated support arm 38 and probe housing 39 are automatically powered to rotate from safe retracted position 41, shown dotted in FIG. 1, to prove test up position 42 and probe test down position 43, all being done by two pressurized fluid cylinders shown in FIG. 2 and described below. Fluid pressure for these cylinders and the roll gap fluid bearing is controlled by three solenoid valves in electro-fluid controls 44 which is fed from dual regulated fluid source 45. A first regulated pressurized fluid cylinder source is supplied over line 46 to two solenoid valves in control device 44 and then over lines 47,48 to the two fluid cylinders that provide probe support arm 38 movements. A second and separately regulated fluid bearing source is supplied over line 49 to the third solenoid valve in control device 44 for delivery to the probe head-to-roll gap fluid bearing. All fluidic devices will be described more fully below.

Limit switches (not shown) in the articulated support arm 38 operate with predetermined movements and provide electrical control signals over line 51 to control device 44 as will also be described below.

Test control panel 52 and grinder control panel 53, both shown in FIG. 6, provide a control and indication means for roll grinder 22 operator to interact with electrofluidic controls 44 over respective control leads 54,55 to initiate automatic controls over testing functions described below. Grinder control panel 53 provides variable speed control signals over line 56 to roll drive motor controller 27, variable speed control signals over line 57 to grinder motor controller 34, and variable speed control signals over line 58 to grinder carriage traverse controller 31, all to provide conventional speed and startstop control functions for their respective powered devices. Grinder carriage 29 traverse is limited according to preselected roll size, either by 137 cm. (54") limit switch 59 action or by 188 cm. (74") limit switch 60 action, both limit switch control signals fed over line 61 to test control panel 52 and on to grinder control panel 53.

As will be described below, articulated probe mechanism 35 has a probe housing 39, one to three nondestructive testing (NDT) probe sensors of either the eddy current type or the ultrasonic type, depending on the user's choice and preference. Also included in probe housing 39 is a temperature sensor. Separate anomoly test signal path(s) and temperature signal path emanate from probe house 39 and are fed over respective lines 62,63 to an appropriate nondestructive test instrument 64,65. Such a test instrument may be of conventional eddy current or ultrasonic 64,65 design.

Turning now to FIGS. 2 to 5, articulated probe mechanism 35 is automatically positioned relative test roll surface 25 by two pressurized fluid power cylinders 66,67 acting against structural components thereof to cause movement. Fluid lines have been omitted for purposes of clarity. Fluid cylinder 66, under control of solenoid valve 68, receives first source 46 cylinder regulated fluid pressure over pipe 69 and acts against stationary butt plate 70 and bellcrank 71 on spindle 37 to cause spindle 37 and articulated support arm 38 to rotate about spindle vertical axis 72. When fluid cylinder 66 is extended, articulated support arm 38 is rotated 90° to the safe retracted position 41 shown in FIG. 1 but not FIG. 2, support arm 38 being in the probe test up position 42. When fluid cylinder 66 is retracted, articulated support arm 38 is rotated to the probe test up position 42 shown in FIG. 2.

Fluid cylinder 67, under control of solenoid valve 73, also receives first regulated pressurized fluid cylinder source 46 preset by valve 46A over pipe 74 and acts against yoke 75 bolted onto spindle 37, through arm height adjustment line 76, forked arm end 77 and fork pin 78 to raise and lower the position of arm axis 79 between probe test up position 42 shown dotted and probe test down position 43 shown solid in FIG. 2. When fluid cylinder 67 is retracted, articulated probe support arm 38 is in the probe test up position 42, shown dotted in FIG. 2, and when extended arm 38 is in the probe test down position 43.

Fluid cylinder 66,67 travel distance is controlled by two corresponding limit switches 80,81, respectively, which provide electrical control signals over leads 83,84 to the coils of solenoid valves 68,73 in electro-fluidic controls 44. Limit switch 80 is adjusted so that cylinder 66 rotates spindle 37 90° between the safe retracted position 41 of articulated support arm 38 and the probe test up position 42. Limit switch 81 is adjusted so that cylinder 67 raises and lowers the articulated support arm 38 in the test position between up and down probe test positions 42,43, respectively.

When the articulated support arm 38 is in the probe test down position 43, a third limit switch 82 provides an electrical control signal through leads 85 to solenoid valve 86 which controls the on-off flow of the second regulated pressure fluid bearing supply 49 over pipe 87 to probe housing 39. The amount of second regulated pressure for the fluid bearing is preset at regulating valve 49A by the grinder operator so as to maintain a constant predetermined dimension at roll gap fluid bearing 88 between probe housing 39 and test roll surface 25. Pressure switch 86A provides a fluid pressure electrical indicator signal over conduit 54 to test control panel 52 described below.

FIGS. 3–5 show the detailed construction of probe housing 39, and universal mount 40 at the end of articulated support arm 38 which enables probe housing 39 to automatically maintain a uniform dimension in fluid bearing roll gap, regardless of irregularities in test roll surface 25 or those that may be caused by the grinder carriage traverse relative test roll surface 25.

Universal mount 40 has three-degrees of slip and rotational movement for attaching probe head 39 to the end of support arm 38. Included in universal mount 40 is a positioning clamp 89 for presetting an arcuate support position around the end of a tubular member of support arm 38. Extending laterally from position clamp 89 is support shaft 90 slip fitted through a bearing hole (not shown) through the top of an inverted hollowed out U-shaped joint member 91 and held on rotatably by snap ring 92. U-shaped joint member 91 rotation on shaft 90 is limited to a predetermined arcuate movement by stop clamp 93.

Downward extending flanges 94,95 on member 91 contain ball bearings 96,97, respectively, through which nut and bolt assemblies 98,99 provide for arcuate movement thereabout at 90° to the shaft 90-member 91 rotation movement, thus furnishing the second degree of freedom of movement. Probe housing 39 is provided with upwardly extending flanges 100,101 located inside flanges 94,95, respectively, and having an end slidably adapted to be pivotally secured to bolt heads of assemblies 98,99, thus providing vertical adjustment capabilities as the third degree of freedom of movement of probe housing 39.

The fluid bearing for probe housing 39 is provided by extending fluid bearing regulated pressure pipe 87 to eight-port manifold 102, which is held on the end of support arm 38 by clamp 103. Each outlet on manifold 102 is connected typically through flexible tubing 104 to eight fluid ports 105 to 112 bored through probe head 39 perpendicular to arcuate test surface 113 to communicate with test roll surface 25. Arcuate test surface 113 is machine contoured to match the radius of test roll surface 25 plus a predetermined dimension equal to roll gap fluid bearing roll 88. If during testing any tilting of probe head 39 should occur, a stop cock (not shown) may be connected in each flexible tubing at manifold 102 and adjusted so that individual fluid flow to each fluid port 105–112 when properly balanced will automatically maintain the predetermined dimension uniformly throughout roll gap fluid bearing 88. Maintaining this uniform roll gap is an important parameter in nondestructive testing whether using either eddy current or ultrasonic NDT methods if accurate and reliable results are to be obtained using probe housing 39 or other designs. Nevertheless, the roll gap fluid bearing 88 is a superior arrangement compared to prior art wearing block used therein.

When probe mechanism 35 is automatically positioned over test roll surface 25 as described above, the one-to-three NDT probe sensors therein are each capable of generating an anomoly test signal when detecting defects in test roll surface 25 as roll 23,24 is rotated. Probe housing 39 is shown having NDT probe sensors 114,115,116, each of which are threadably secured in staggered bores drilled on separate axis having the same radius as that of test roll surface 25 to be inspected. Each NDT probe sensor 114,115,116 corresponds to probe channel No. 1,2,3, respectively, and may be of eddy current design to operate with NDT test instrument 64 Each such eddy current probe 114,115,116 may have a single sensor coil located near arcuate test surface 113, or may have on additional reference coil spaced away from surface 113.

Alternatively a single utlrasonic probe sensor 117, located in probe housing 39 at the same bore as eddy current probe sensor 115 and arcuate test surface 113, may be operatively associated with NDT test instrument 65. Ultrasonic probe sensor may be of a single alternate transmit/receive crystal design or have dual crystals to perform separate transmit and receive functions.

Eddy current type of probe sensors 114,115,116 each generate an eddy current anomoly test signal characterized by a complex analog signal waveform representing a test roll surface 25 defect anywhere along a circumferential scanning path along test roll surface 25. These eddy current anomoly test signals are fed over corresponding lines 118,119,120 to NDT test instrument 64. Similarly, ultrasonic probe sensor 117 generates an ultrasonic anomoly test signal characterized by a variable amplitude pulse signal representing a test roll surface 25 defect as with the eddy current probes. The ultrasonic anomoly test signal is alternately fed over line 121 to NDT test instrument 65.

In some installations the ambient temperature of probe housing 39, roll gap fluid bearing 88 and/or test roll surface 25 may vary beyond calibration or other acceptable limits, particularly on test roll surface 25 during or immediately after roll grinding procedures. For these reasons, probe housing 39 is also provided with probe temperature sensor 122 located adjacent the probe sensors 114, 115,116 or 117. Probe temperature sensor signal is fed over line 123 to compensate a modified NDT test instrument 64,65 for variations in the corresponding anomoly test signals due to such temperature variations. Otherwise, if any of the aforesaid temperature variations does not significantly affect defect test signals, then temperature sensor 122 and line 123 may be eliminated from probe lead 39.

Turning to FIG. 5, there is shown in isometric view the component parts of probe housing 39 and universal mount 40 located at the end of support arm 38. Provisions are also shown for artificial calibrator 124 to be inserted at arcuate test surface 113 in place of test roll 23,24, adjacent their roll test surface 25. Artificial calibrator 124 has a rectangular flat base 125, two upright members 126,127 at opposite sides of base 125, and a cast steel roll segment 128 secured to and between upright members 126,127 and to base 125. Cast steel roll segment 128 has the same metallurgy as rolls 23,24 and is machined with an artificial arcuate test surface 129 to correspond to the contour of test roll surface 25 radius. Machined in artificial test surface 129 are three test grooves 130,131,132 of known characteristic defect and these grooves correspond to the location of NDT probe sensors 116, 115 or 117, 114 shown in FIG. 3. Artificial calibrator 124 is held with artificial arcuate test surface 129 against arcuate test surface 113 in probe housing 39 by a pair of attachment clips 133 with an opening slipped over each nut end of device 98,99 and held biased in position with two attachment springs 134. After artificial calibration procedures are completed, calibration device 124 is removed from probe head 39.

Not shown is a shim of the same dimension as roll gap fluid bearing 88 which is placed between the two arcuate test surfaces 113 and 129. This is done to completely duplicate as near as possible a probe calibration setup resembling actual roll test conditions. The use of artificial calibrator 124 is a preferred embodiment for calibrating the NDT testing system.

Reference will now be made to FIGS. 1 and 6 for the description of test control panel 52 and grinder control panel 53, both of which are provided so that the grinder operator may perform the NDT testing of rolls 23,24 without having any skills in these methods of testing. Test control panel 52 includes a series of indicator lights 135–140 that indicate the sequential status of respective functions including 135 test power on, 136 roll size selection made, 137 fluid bearing pressure on, 138 roll 23,24 up to preset work speed, 139 grinder carriage 29 up to preset traverse speed and 140 grinder carriage 29 traverse at preselected roll size as determined by limit switches 59,60. Test control panel 52 also includes roll size selector switch 141 having 137 cm. (54") and 188 cm. (74") preset positions, and a test mode selector switch 142 having 1ST TEST and RETEST preset positions, both of which are preset by the grinder operator before automatic testing may proceed.

Test control panel 52 includes three pushbuttons for the grinder operator to initiate internal control devices, which together with solenoid valves 68,73,86 in electro-fluid controls 44, cooperate to automatically position probe mechanism 35 over test roll surface 25 and maintain roll gap fluid bearing 88 as described above. STOP pushbutton 143 will interupt and stop a test procedure at any sequential step and deenergize solenoid valves 68,73,86 so that fluid cylinders 66,67 return articulated support arm 38 to the safe retracted position 41 with probe housing 39 in the probe test up position 42 when retracted, fluid bearing flow is stopped in probe housing 39. START pushbutton 144 reenergize solenoid valve 68 and causes fluid cylinder 66 to swing articulated support arm 39 90° to the probe test up position 42. TEST pushbutton 145 energizes solenoid valve 73 and causes support arm 38 to lower to horizontal probe test down position 43. At the time support arm 38 reaches the probe test down position 43, solenoid valve 86 is energized and causes the fluid bearing flow to appear at probe head 39 when in the test down position 43. This automatically establishes the predetermined dimension of roll gap fluid bearing 88 and prepares for defect detection along the portions of roll test surface 25 to be inspected. Support arm 38 may be raised to the probe test up position 42 for roll inspection or other purposes and the fluid bearing flow ceased by pressing START pushbutton 144. A return to the testing position will be accomplished thereafter by again pressing the TEST pushbutton 145.

Grinder control panel 53, which interacts with test control panel 52, includes only those control functions associated with grinder operator controls that are required for explanation of the present invention, but not necessarily all grinder control function avaiable to the grinder operator. Roll drive START and STOP pushbuttons 146,147 and work speed control preset rheostat 148 provide corresponding control and variable speed control signals on line 56 to and from roll drive motor controller 27. Grinder carriage START and STOP pushbuttons 149,150 and traverse speed control preset rheostat 151 provide corresponding control and variable speed control signals on line 58 to and from grinder carriage traverse controller 31. Grinder wheel START and STOP pushbuttons 152,153 and wheel speed control preset rheostat 154 also provide corresponding control and variable speed control signals on line 57 to and from grinder motor controller 34.

Also included in grinder control panel 53 are the source of indicator signals fed over line 55 to test control panel 52 for roll work speed indicator 138 and traverse speed indicator 139 when their respective drive controllers 27,31 have caused their drive motor to reach the speed preset by rheostats 148,151. The traverse limit indicator 140 on test control panel 52 lights up when grinder carriage 29 reaches limit switch 59 or 60 after being preselected by roll size selector switch 141 also on the test control panel 52.

When the automatic probe positioning procedure is completed to the probe test down position 43, the anomoly test signals generated by eddy current probe sensors 114,115,116, or alternatively the ultrasonic probe sensor 117, representing test roll surface 25 defects, are fed from articulated probe mechanism 35 to nondestructive test instrument 64,65 shown in FIG. 1. Similarly, if temperature sensor 122 was included in probe housing 39 with either eddy current or ultrasonic type of test probe sensor, then the temperature signal will be fed separately from articulated probe mechanism 35 over line 63 to nondestructive test instrument 64,65 shown in FIG. 1. Due to interlocking control functions of control panels 52,53, these anomoly test signal(s) and temperature signal are generated, in probe test down position 43, along the entire length of preselected roll 23,24 when carriage 29 traverses from either right-to-left or left-to-right of the grinder operator, and will continue to be generated until a complete scan is made in one direction of test roll 23,24.

Defects are displayed on an internal meter, or display, of nondestructive test instrument 64,65. If these defects exceed a predetermined magnitude alarm device 155 will be activated.

When defects are found on test roll surface 25, either plunge grinding or traverse refinishing of the entire test roll surface 25 will be necesssary and require use of grinder apparatus 22 by the roll grinder operator. After this is done, roll surface 25 defect testing may be repeated, if desired, by the grinder operator turning roll test mode selector switch 142 on test control panel 52 to the RETEST position momentarily and repeating the foregoing defect testing and grinding or refinishing procedures the number of times required to accept or reject test roll 23,24. Concluding either the TEST mode or the RETEST mode of defect testing at the end of a roll length traverse will automatically return probe housing 39 to the test probe test up position 42. Pressing the test STOP pushbutton 143 will automatically return probe housing 39 to the safe retracted probe position 41.

I claim:

1. A nondestructive probe mechanism for testing roll surface conditions of a rolling mill roll rotatable in a test fixture and operable with a grinder carriage moveable substantially parallel to and lengthwise of the test roll longitudinal axis, said probe mechanism comprising:

(a) articulated probe structure means mountable on the grinder carriage, said structure means comprising:
 1. a carriage-mounted base member with upright support,
 2. a spindle rotatable about the upright support,
 3. a moveable support arm pivotally attached to the spindle with a free end positionable over at least the test surface,
 4. a universal mount on the free end of the support arm providing attachment means with at least one axis of movement,
 5. a nondestructive test probe housing attached to the universal mount attachment means and wherein a probe sensor of either eddy current or ultrasonic design generates an anomoly test signal when aligned with the test roll surface, and
 6. said probe housing being modified to include pressurized fluid bearing means capable of maintaining a probe housing-to-test roll gap;

(b) means for automatically positioning the test probe housing including:
 1. first and second fluid pressure responsive means cooperating with the spindle and the support arm to position the probe housing in a safe retracted position related away from the test roll, a probe test up position and a probe test down position over the test roll surface, all in response to corresponding position control signals,
 2. a first pressurized fluid source adjusted to maintain a constant fluid bearing roll gap, and
 3. a second pressurized fluid source for said fluid pressure responsive means;

(c) control means for producing the corresponding position control signals in response initially to a command.

2. The apparatus of claim 1 wherein the control means includes a test control panel initiated by an operator for controlling automatic probe housing positioning.

3. The apparatus of claim 1 wherein the control means includes a test control panel initiated by an operator for controlling automatic probe housing positioning and another control panel initiated by the same operator for controlling test roll rotation and carriage movement.

* * * * *